United States Patent [19]

Zondler et al.

[11] 4,113,669
[45] Sep. 12, 1978

[54] POLYMERS FLAMEPROOFED WITH 1,2-OXAPHOSPHOLANES

[75] Inventors: Helmut Zondler, Bottmingen; Emil Saladin, Augst; Rudolf Kirchmayr, Münchenstein, all of Switzerland

[73] Assignee: Ciba-Geigy Corporation, Ardsley, N.Y.

[21] Appl. No.: 806,044

[22] Filed: Jun. 13, 1977

Related U.S. Application Data

[60] Division of Ser. No. 615,455, Sep. 22, 1975, Pat. No. 4,045,518, which is a continuation-in-part of Ser. No. 499,888, Aug. 23, 1974, abandoned.

[30] Foreign Application Priority Data

Sep. 7, 1973 [CH] Switzerland ............ 12890/73
May 21, 1974 [CH] Switzerland ............ 6981/74
Jul. 29, 1974 [CH] Switzerland ............ 10465/74

[51] Int. Cl.² ............................................. C08K 5/53
[52] U.S. Cl. ...................................... 521/108; 106/177; 260/45.8 A; 260/45.8 R; 260/45.8 RW; 260/297 P; 260/329 P; 260/346.11; 521/906
[58] Field of Search ............... 260/45.8 R, 2.5 AJ, 260/297 P, 329 P, 346.11; 106/177

[56] References Cited

U.S. PATENT DOCUMENTS

| 3,668,302 | 6/1972 | Boland et al. ............ 106/177 |
| 3,849,368 | 11/1974 | Anderson et al. ............ 260/45.8 R |
| 3,887,656 | 6/1975 | Shim ............ 260/2.5 AJ |
| 3,970,726 | 7/1976 | Batorewicz ............ 260/2.5 AJ |
| 4,001,176 | 1/1977 | Clovis et al. ............ 260/45.8 R |
| 4,024,207 | 5/1977 | Biehler et al. ............ 260/2.5 AJ |

Primary Examiner—Donald E. Czaja
Assistant Examiner—R. A. White
Attorney, Agent, or Firm—Luther A. R. Hall

[57] ABSTRACT

2-Oxo-2-alkoxy-5-dialkylphosphono-1,2-oxaphospholanes of the formula

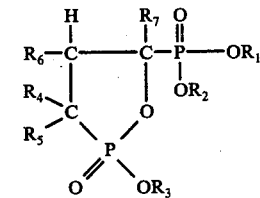

in which $R_1$ to $R_7$ are hydrocarbon radicals can be prepared from $\alpha,\beta$-unsaturated ketones and 2 or more moles of a dialkyl phosphite. Obviously $\gamma$-ketophosphonates are intermediates of this reaction, as these compounds react with 1 or more moles of dialkyl phosphite in yielding the oxaphospholanes too. Both reactions are promoted by alkaline catalysts.

The new oxaphospholane derivatives are considerably stable against thermal decomposition. They are compatible with polymeric materials and can be used as flame protecting agent for plastics and resins, for example, in polyurethane foams.

11 Claims, No Drawings

POLYMERS FLAMEPROOFED WITH 1,2-OXAPHOSPHOLANES

This is a divisional of application Ser. No. 615,455, filed Sept. 22, 1975, now U.S. Pat. No. 4,045,518, issued Aug. 30, 1977, which is a continuation-in-part of application Ser. No. 499,888, filed Aug. 23, 1974, now abandoned.

This invention pertains to new 1,2-oxaphospholane-5-phosphonic acid esters, a process for their manufacture, a method of using them as flameproofing agents for thermoplastic polymers, polyurethanes, cellulose and cellulose derivatives and also the substrates protected by them.

The new compounds have the general formula I

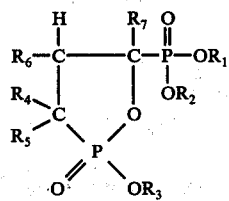

(I)

wherein each of $R_1$, $R_2$ and $R_3$ independently represents a monovalent aliphatic, cycloaliphatic or araliphatic radical or a tetrahydrofurfuryl radical, each of $R_4$, $R_5$ and $R_6$ independently represents hydrogen, alkyl or a monovalent aromatic or heteroaromatic radical, and $R_7$ represents alkyl or a monovalent aromatic or heteroaromatic radical.

A monovalent aliphatic radical represented by $R_1$, $R_2$ or $R_3$ can be a linear or branched alkyl or alkenyl radical which is unsubstituted or substituted by halogen or alkoxy groups.

Examples of $R_1$, $R_2$ or $R_3$ when alkyl of 1 to 18 carbon atoms are methyl, ethyl, isopropyl, n-butyl, 2-ethylhexyl, isooctyl, n-dodecyl and n-octadecyl.

Examples of $R_1$, $R_2$ or $R_3$ when alkenyl of 3 to 18 carbon atoms are allyl, methallyl and oleyl.

When $R_1$, $R_2$ or $R_3$ is haloalkyl of 2 to 18 carbon atoms, such groups are 2-chloroethyl, 2-bromoethyl and 2,3-dibromopropyl.

When $R_1$, $R_2$ or $R_3$ is alkoxyalkyl of not over 18 carbon atoms, such groups include 2-ethoxyethyl, 2-methoxyethyl, 2-n-butoxyethyl and 2-methoxypropyl.

Where $R_1$, $R_2$ or $R_3$ represent a monovalent cycloaliphatic radical, such groups are cycloalkyl of 5 to 8 carbon atoms such as cyclopentyl, cyclohexyl and cyclooctyl.

When $R_1$, $R_2$ or $R_3$ represent a monovalent araliphatic radical, examples are aralkyl of 7 to 15 carbon atoms or aralkyl of 7 to 15 carbon atoms substituted by halogen or alkoxy groups of 1 to 4 carbon atoms such as benzyl, 2-methylbenzyl, α,α-dimethylbenzyl, β-phenylethyl, 4-chlorobenzyl or 4-methoxybenzyl.

Alkyl radicals represented by $R_4$, $R_5$, $R_6$, or $R_7$ can be linear or branched alkyl radicals, e.g., methyl, ethyl, isopropyl, tert-butyl, n-hexyl, 2-ethylhexyl, n-octyl, isooctyl, n-dodecyl or n-octadecyl. An aromatic radical represented by these same substituents can be phenyl, naphthyl or diphenylyl radical which is unsubstituted or which is substituted by halogen, alkyl and/or alkoxy groups. A monovalent heteroaromatic radical represented by these same substituents can be heteroaromatic radical which is unsubstituted or which is substituted by halogen, alkyl, phenyl and/or alkoxy groups, e.g., corresponding radicals of furan, thiophene, cumarone, dibenzofuran, pyridine, quinoline or carbazole.

Preferred compounds are those of the formula I wherein each of $R_1$, $R_2$ and $R_3$ independently represents alkyl with 1 to 18 carbon atoms, haloalkyl or alkoxyalkyl having not more than 18 carbon atoms, alkenyl with 3 to 18 carbon atoms, tetrahydrofurfuryl, cycloalkyl with 5 to 8 carbon atoms, aralkyl with 7 to 15 carbon atoms or aralkyl with altogether 7 to 15 carbon atoms which is substituted by halogen and/or alkoxy groups of 1 to 4 carbon atoms, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups with 1 to 4 carbon atoms, or represents furyl, thienyl or pyridyl, $R_6$ represents hydrogen, methyl or phenyl, and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms, or represents furyl, thienyl or pyridyl. By halogen is meant in this context fluorine, chlorine or bromine.

Other preferred compounds have the formula Ia

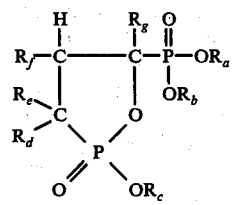

(Ia)

wherein
each of $R_a$, $R_b$ and $R_c$ independently represents alkyl of 1 to 18 carbon atoms, haloalkyl with 2 to 18 carbon atoms, alkoxyalkyl having not more than 18 carbon atoms, alkenyl with 3 to 18 carbon atoms, cycloalkyl with 5 to 8 carbon atoms, aralkyl with 7 to 15 carbon atoms, aralkyl with altogether 7 to 15 carbon atoms which is substituted by halogen or alkoxy groups of 1 to 4 carbon atoms, or is tetrahydrofurfuryl, $R_d$ represents hydrogen or methyl, $R_e$ represents hydrogen, alkyl with 1 to 8 carbon atoms, aryl with 6 to 10 carbon atoms, aryl with 6 to 10 carbon atoms which is substituted by halogen, alkyl or alkoxy groups with 1 to 4 carbon atoms, or furyl, thienyl or pyridyl, and with the proviso that when $R_e$ is hydrogen or alkyl, none of $R_a$, $R_b$ or $R_c$ can be alkyl, $R_f$ represents hydrogen, methyl or phenyl, and $R_g$ represents alkyl with 1 to 8 carbon atoms, aryl with 6 to 10 carbon atoms, aryl with 6 to 10 carbon atoms which is substituted by halogen, alkyl or alkoxy with 1 to 8 carbon atoms, or is furyl, thienyl or pyridyl.

By halogen is meant in this context fluorine, chlorine or bromine.

Compounds of the formula I which constitute a specially preferred class of these compounds are those wherein each of $R_1$ and $R_2$ independently represents a monovalent aliphatic, cycloaliphatic or araliphatic radical, $R_3$ is the same as either $R_1$ or $R_2$, each of $R_4$, $R_5$ and $R_6$ independently represents hydrogen, alkyl or a monovalent aromatic or heteroaromatic radical, and $R_7$ represents alkyl or a monovalent aromatic or heteroaromatic radical.

To this class of compounds belong the compounds of the formula I wherein each $R_1$ and $R_2$ independently represents alkyl with 1 to 18 carbon atoms, haloalkyl or alkoxyalkyl having not more than 18 carbon atoms, alkenyl with 3 to 18 carbon atoms, tetrahydrofurfuryl, cycloalkyl with 5 to 8 carbon atoms, aralkyl with 7 to 15 carbon atoms or aralkyl with altogether 7 to 15 carbon atoms which is substituted by halogen and/or alkoxy groups of 1 to 4 carbon atoms, $R_3$ is the same as either $R_1$ or $R_2$, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups of 1 to 4 carbon atoms, or represents furyl, thienyl or pyridyl, $R_6$ represents hydrogen, methyl or phenyl, and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms, or represents furyl, thienyl or pyridyl.

Other specially preferred compounds are those of formula Ia wherein each of $R_a$ and $R_b$ independently denotes alkyl of 1 to 18 carbon atoms, haloalkyl of 2 to 18 carbon atoms, alkoxyalkyl having not more than 18 carbon atoms, alkenyl with 3 to 18 carbon atoms, cycloakyl with 5 to 8 carbon atoms, aralkyl with 7 to 15 carbon atoms or aralkyl with altogether 7 to 15 carbon atoms which is substituted by halogen or alkoxy groups of 1 to 4 carbon atoms, or is tetrahydrofurfuryl; $R_c$ is the same as either $R_a$ or $R_b$; $R_d$ represents hydrogen or methyl; $R_e$ represents hydrogen, alkyl with 1 to 8 carbon atoms, aryl with 6 to 10 carbon atoms, aryl with 6 to 10 carbon atoms which is substituted by halogen, alkyl or alkoxy of 1 to 4 carbon atoms, or is furyl, thienyl or pyridyl, and with the proviso that when $R_e$ is hydrogen or alkyl, none of $R_a$, $R_b$ or $R_c$ can be alkyl; $R_f$ represents hydrogen, methyl or phenyl; and $R_g$ represents alkyl with 1 to 8 carbon atoms, aryl with 6 to 10 carbon atoms, aryl with 6 to 10 carbon atoms which is substituted by halogen, alkyl or alkoxy with 1 to 8 carbon atoms, or is furyl, thienyl or pyridyl, By halogen is meant also in this context chlorine or bromine.

Particularly preferred compounds of the formula I are those wherein $R_1$, $R_2$ and $R_3$ are identical and represent linear or branched alkyl radical with 1 to 8 carbon atoms, alkoxyalkyl with 3 to 6 carbon atoms, 2-chloroethyl, 2-bromoethyl, alkenyl with 3 to 4 carbon atoms, cyclohexyl, benzyl or tetrahydrofurfuryl, $R_4$ represents hydrogen or methyl, $R_5$ represents hydrogen, methyl, ethyl, phenyl, naphthyl; phenyl or naphthyl substituted with 1 to 5 chlorine or bromine atoms; p-tolyl, xylyl, p-anisyl, 2-furyl, 2-thienyl or pyridyl, $R_6$ represents hydrogen or methyl, and $R_7$ represents methyl, ethyl, phenyl, phenyl substituted with 1 to 5 chlorine or bromine atoms; p-tolyl, xylyl, p-anisyl, 2-furyl or 2-thienyl.

Other particularly preferred compounds of formula Ia are those wherein $R_a$, $R_b$ and $R_c$ are identical and represent alkyl of 1 to 8 carbon atoms, alkoxyalkyl with 3 to 6 carbon atoms, alkoxyalkyl with 3 to 6 carbon atoms, 2-chloroethyl, 2-bromoethyl, alkenyl with 3 to 4 carbon atoms cyclohexyl, benzyl or tetrahydrofurfuryl; $R_d$ represents hydrogen or methyl; $R_e$ represents hydrogen, methyl, ethyl, phenyl, naphthyl; phenyl or naphthyl substituted by 1 to 5 chlorine or bromine atoms; p-tolyl, p-anisyl, xylyl, 2-furyl, 2-thienyl or 2-pyridyl, and with the proviso that when $R_e$ is hydrogen, methyl or ethyl, $R_a$, $R_b$ and $R_c$ cannot be alkyl; $R_f$ represents hydrogen or methyl; and $R_g$ represents methyl, ethyl, phenyl, phenyl substituted with 1 to 5 chlorine or bromine atoms, p-tolyl, xylyl, p-anisyl, 2-furyl or 2-thienyl, The surprising discovery has been made that it is possible to manufacture the compounds of the formula Ia, in which $R_c$ is the same as $R_a$ or $R_b$, by a novel process which comprises reacting an $\alpha,\beta$-unsaturated ketone of the formula II

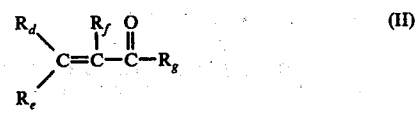

with at least 2 moles of a phosphite of the formula III

in the presence of a base, with or without the addition of a solvent.

Examples of $\alpha,\beta$-unsaturated ketones of the formula II are methyl vinyl ketone, ethyl vinyl ketone, phenyl vinyl ketone, mesityl oxide, methyl isopropenyl ketone, benzalacetone, benzalacetophenone or 4-chlorobenzalacetone. Such ketones can be manufactured by known methods, for example, by condensation of the appropriate methyl ketones with aldehydes or ketones. Other $\alpha,\beta$-unsaturated ketones useful in this invention include $\alpha$-ionone, $\beta$-ionone, 4-methoxy-3-buten-2-one, 3-penten-2-one, isophorone and phorone.

The phosphites of the formula III are known compounds of industrial availability. Examples thereof are dialkyl phosphites, e.g., dimethyl, diethyl or dioctyl phosphite, dicycloalkyl phosphites, e.g., dicyclohexyl phosphite, diaralkyl phosphites, e.g., dibenzyl phosphite, and mixed phosphites, e.g., methyl butyl phosphite, methyl benzyl phosphite or isopropyl cyclohexyl phosphite.

In the reaction there are used 2 moles, preferably 2.5 to 3.5 moles, of a compound of the formula III for each mole of the compound of the formula II.

Examples of bases which catalyze the reaction are principally alkali metals, alkali metal or alkaline earth metal alkoxides, alkali metal amides and hydrides. Particularly effective are the metals sodium and potassium, sodium ethoxide, sodium methoxide, potassium tert-butoxide, lithium amide and calcium hydride; but the two metals, sodium and potassium, are particularly suitable for the purpose. Normally, catalytic amounts of these bases suffice to initiate the reaction. It is sometimes advantageous to add further amounts of base during the reaction.

If the process according to the invention is carried out with the addition of a solvent, then suitable solvents are primarily hydrocarbons, e.g., benzene, toluene, xylene, ligroin, hexane or heptane, also alcohols, e.g., methanol, ethanol or isopropanol, or ethers, e.g., diethyl ether, dioxane or tetrahydrofuran.

The reaction can be carried out by dissolving the ketone of the formula II and adding dropwise a portion of the phosphite of the formula III and the base. Upon onset of the reaction, the remainder of the phosphite and, if necessary, further amounts of base are added by gradual amounts. It is also possible to premix the phosphite with the catalyst and to add the ketone of the formula II dropwise.

In another embodiment, the compounds of the formulas II and III and optionally the solvent are first mixed and then the base, which can also be dissolved in the solvent, is added to this mixture and the reaction is brought to completion by heating.

The oxaphospholanes of the formula Ia are isolated by customary methods, for example, by distillation. Desirably the base is neutralized before the isolation by an equivalent amount of an acid, for example, acetic acid.

The reaction of dialkyl phosphites with α,β-unsaturated ketones has already been thoroughly investigated by various experts. It has hitherto been considered the rule that in the reaction only 1 mole of phosphite is added to the double bond forming the γ-ketophosphonates (see Houben-Weyl, Methoden der Organischen Chemie, vol. 12/1, pages 465–467, G. Thieme Verlag, Stuttgart, 1963). If diphosphonates were also obtained, these occurred in moderate yield in addition to the monophosphonates (A. N. Pudovik, *Zhurnal Obshch. Khim.*, 22, 1371, (1952); *Chem. Abstr.* 47, 4837, (1953). It was therefore surprising that in the process described herein 2 moles of phosphite are added easily. It was furthermore surprising that the γ-phosphono-α-hydroxyphosphonates evidently formed as intermediate cyclize under the reaction conditions rapidly and virtually completely to give the 1,2-oxaphospholane-5-phosphonates.

The reaction of 1 mole of acetylacetone, α,β-diketone, with 2 moles of diethyl phosphite was reported by B. A. Arbuzov et al, *Izv. Akad. Nauk. SSSR*, Ser Khim 12, 2757 (1971) to give 2-oxo-2-ethoxy-3-hydroxy-3,5-dimethyl-5-diethylphosphono-1,2-oxaphospholane. This compound, although somewhat related to the compounds of this invention, possesses quite different chemical properties due to the presence of the 3-hydroxy group, and can undergo a variety of chemical reactions unavailable for the instant compounds.

It has furthermore been found that oxaphospholane derivatives of the formula I can also be manufactured from the known γ-ketophosphonates by addition of dialkyl phosphites. This is an indication that the reaction discussed above probably proceeds via the stage of the γ-ketophosphonates. It is therefore possible to carry out the reaction in two partial steps, the first being the known addition of 1 mole of phosphite to α,β-unsaturated ketones to form the γ-ketophosphonates and the second being the reaction with a second mole of phosphite to form the oxaphospholanes. This second step is just as surprising and novel as the single step main process.

The invention therefore also provides a process for the manufacture of compounds of the formula Ia, which comprises reacting a compound of the formula IV

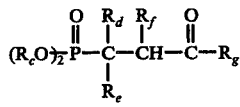

(IV)

with at least one mole of phosphite of the formula III in the presence of a base, with or without the addition of a solvent. In the formula IV, the substituents $R_c$ to $R_g$ have the same meanings assigned to them as in respect of the compounds of the formula Ia. The catalysts and solvents suitable for use in this process are the same as those for the single step main process described hereinbefore, and the reaction and isolation of the products are carried out in the same way.

This modification is principally of importance for the manufacture of those compounds of the formula Ia in which $R_c$ is different from $R_a$ and $R_b$.

Examples of individual compounds of formula I are the following 1,2-oxaphospholane derivatives:

2-oxo-2-methoxy-5-ethyl-5-dimethylphosphono-1,2-oxaphospholane 2-oxo-2-ethoxy-5-ethyl-5-diethylphosphono-1,2-oxaphospholane 2-oxo-2-methoxy-5-methyl-5-dimethylphosphono-1,2-oxaphospholane 2-oxo-2-ethoxy-5-methyl-5-diethylphosphono-1,2-oxaphospholane 2-oxo-2-isopropoxy-5-methyl-5-diisopropylphosphono-1,2-oxaphospholane 2-oxo-2-ethoxy-3,3,5-trimethyl-5-diethylphosphono-1,2-oxaphospholane 2-oxo-2-isopropoxy-3,3,5-trimethyl-5-diisopropylphosphono-1,2-oxaphospholane 2-oxo-2-butoxy-3,3,5-trimethyl-5-dibutylphosphono-1,2-oxaphospholane 2-oxo-2-(2-ethylhexyloxy)-3,3,5-trimethyl-5-bis-(2-ethylhexyl)-phosphono-1,2-oxaphospholane 2-oxo-2-butoxy-5-methyl-5-dibutylphosphono-1,2-oxaphospholane 2-oxo-2-octoxy-5-methyl-5-dioctylphosphono-1,2-oxaphospholane 2-oxo-2-(2-ethylhexyloxy)-5-methyl-5-bis-(2-ethylhexyl)-phosphono-1,2-oxaphospholane 2-oxo-2-octadecyloxy-5-methyl-5-dioctadecylphosphono-1,2-oxaphospholane 2-oxo-2-methoxy-3,5-dimethyl-5-dimethylphosphono-1,2-oxaphospholane 2-oxo-2-ethoxy-3,5-dimethyl-5-diethylphosphono-1,2-oxaphospholane 2-oxo-2-methoxy-3,4-dimethyl-5-dimethylphosphono-1,2-oxaphospholane 2-oxo-2-ethoxy-3,4-dimethyl-5-diethylphosphono-1,2-oxaphospholane 2-oxo-2-methoxy-3,3,5-trimethyl-5-dimethylphosphono-1,2-oxaphospholane 2-oxo-2-(2-chloroethyloxy)-5-methyl-5-bis-(2-chloroethyl)-phosphono-1,2-oxaphospholane 2-oxo-2-(2-methoxyethyloxy)-5-methyl-5-bis-(2-methoxyethyl)-phosphono-1,2-oxaphospholane 2-oxo-2-benzyloxy-5-methyl-5-dibenzylphosphono-1,2-oxaphospholane 2-oxo-2-(4-chlorobenzyloxy)-5-methyl-5-bis-(4-chlorobenzyl)-phosphono-1,2-oxaphospholane 2-oxo-2-(4-bromobenzyloxy)-5-methyl-5-bis-(4-bromobenzyl)-phosphono-1,2-oxaphospholane 2-oxo-2-methoxy-5-phenyl-5-dimethylphosphono-1,2-oxaphospholane 2-oxo-2-ethoxy-5-phenyl-5-diethylphosphono-1,2-oxaphospholane 2-oxo-2-(2-chloroethoxy)-3,3,5-trimethyl-5-bis-(2-chloroethyl)-phosphono-1,2-oxaphospholane 2-oxo-2-benzyloxy-3,3,5-trimethyl-5-dibenzylphosphono-1,2-oxaphospholane 2-oxo-2-cyclohexyloxy-3,3,5-trimethyl-5-dicyclohexylphosphono-1,2-oxaphospholane 2-oxo-2-methoxy-3-phenyl-5-methyl-5-dimethylphosphono-1,2-oxaphospholane
2-oxo-2-ethoxy-3-phenyl-5-methyl-5-diethylphosphono-1,2-oxaphospholane
2-oxo-2-methoxy-3-(4-chlorophenyl)-5-methyl-5-dimethylphosphono-1,2-oxaphospholane
2-oxo-2-methoxy-3-(4-bromophenyl)-5-methyl-5-dimethylphosphono-1,2-oxaphospholane
2-oxo-2-methoxy-3-(4-methylbenzyl)-5-methyl-5-dimethylphosphono-1,2-oxaphospholane
2-oxo-2-methoxy-3-(4-methoxyphenyl)-5-methyl-5-dimethylphosphono-1,2-oxaphospholane
2-oxo-2-methoxy-3-(furyl-2)-5-methyl-5-dimethylphosphono-1,2-oxaphospholane
2-oxo-2-methoxy-3-(thienyl-2)-5-methyl-5-dimethylphosphono-1,2-oxaphospholane
2-oxo-2-methoxy-3-(pyridyl-2)-5-methyl-5-dimethylphosphono-1,2-oxaphospholane
2-oxo-2-methoxy-3-methyl-5-phenyl-5-dimethylphosphono-1,2-oxaphospholane
2-oxo-2-methoxy-3-methyl-5-(4-chlorophenyl)-5-dimethylphosphono-1,2-oxaphospholane
2-oxo-2-methoxy-3,5-diphenyl-5-dimethylphosphono-1,2-oxaphospholane
2-oxo-2-ethoxy-3,5-diphenyl-5-diethylphosphono-1,2-oxaphospholane
2-oxo-2-methoxy-3-(4-chlorophenyl)-5-phenyl-5-dimethylphosphono-1,2-oxaphospholane
2-oxo-2-methoxy-3,5-bis-(4-chlorophenyl)-5-dimethylphosphono-1,2-oxaphospholane
2-oxo-2-methoxy-3-phenyl-5-(4-chlorophenyl)-5-dimethylphosphono-1,2-oxaphospholane
2-oxo-2-methoxy-3-(4-methylphenyl)-5-phenyl-5-dimethylphosphono-1,2-oxaphospholane
2-oxo-2-methoxy-3-(4-methoxyphenyl)-5-phenyl-5-dimethylphosphono-1,2-oxaphospholane
2-oxo-2-methoxy-3-phenyl-5-(4-methylphenyl)-5-dimethylphosphono-1,2-oxaphospholane
2-oxo-2-methoxy-3,5-diphenyl-5-dimethylphosphono-1,2-oxaphospholane
2-oxo-2-allyloxy-3,3,5-trimethyl-5-diallylphosphono-1,2-oxaphospholane
2-oxo-2-tetrahydrofurfuryl-3,3,5-trimethyl-5-di-(tetrahydrofurfuryl)phosphono-1,2-oxaphospholane The compounds of the formula I are outstanding flameproofing agents for thermoplastic polymers, polyurethanes, cellulose and also for cellusose derivatives. It has long been known that phosphorus-containing compounds can be used as flameproofing agents for polymers, but it is normally necessary to use the phosphorus compounds in high concentrations, which results as a rule in some deterioration of the physical properties of the polymers.

The surprising discovery has now been made that the new 1,2-oxaphospholanes of the formula I impart an adequate flame resistance to the polymers even in relatively low concentrations. Moreover, on account of their considerable heat stability, they have only a minute influence on the physical properties of the substrates. Further, they are also usable in reactive systems, such as in polyurethane foams, which both in their manufacture and use, are highly sensitive towards additives.

Examples of thermoplastic polymers which can be flame-protected with the compounds of the formula I are:

1. Polymers wich are derived from singly or doubly unsaturated hydrocarbons, such as polyolefins, e.g., polyethylene, polypropylene, polyisobutylene, polymethylbutene-1, polymethylpentene-1, polybutene-1, polyisoprene, polybutadiene, polystyrene, polyisobutylene, copolymers of the monomers from which the cited homopolymes are derived, such as ethylene-propylene copolymes, propylene-butene-1 copolymers, propylene-isobutylene copolymers, styrene-butadiene copolymers, and terpolymers of ethylene and propylene with a diene, e.g., hexadiene, dicyclopentadiene or ethyldene norbornene; mixtures of the above mentioned homopolymers, e.g., mixtures of polypropylene and polyethylene, polypropylene and polybutene-1, polypropylene and polyisobutylene.

2. Halogen-containing vinyl polymers, e.g., polyvinyl chloride, polyvinylidene chloride, polyvinyl fluoride, but also polychloroprene and chlorinated rubbers.

3. Polymers which are derived from $\alpha,\beta$-unsaturated acids and derivatives thereof, e.g., polyacrylates and polymethacrylates, polyacrylamides and polyacrylonitrile and copolymers thereof with other vinyl compounds, such as acrylonitrile/butadiene/styrene, acrylonitrile/styrene and acrylonitrile/styrene/acrylic ester copolymers.

4. Polymers which are derived from unsaturated alcohols and amines and their acyl derivatives or acetals, such as polyvinyl alcohol, polyvinyl acetate, polyvinyl stearate, polyvinyl benzoate, polyvinyl maleate, polyvinyl butyral, and copolymers thereof with other vinyl compounds, e.g., ethylene/vinyl acetate copolymers.

5. Polyacetals, e.g., polyoxymethylene and polyoxyethylene, and also those polyoxymethylenes that contain ethylene oxide as comonomer.

6. Polyphenylene oxides.

7. Polycarbonates.

8. Polysulfones.

9. Polyamides and copolyamides which are derived from diamines and dicarboxylic acids and/or aminocarboxylic acids or from the corresponding lactams, e.g., polyamide 6, polyamide 6/6, polyamide 6/10, polyamide 11, and polyamide 12.

10. Polyesters which are derived from dicarboxylic acids and dialcohols and/or the corresponding lactones, e.g., polyethylene terephthalate, polybutylene terephthalate, polycyclohexane-1,4-dimethylene terephthalate.

The flameproofing of cellulose and cellulose derivatives is possible in those cases where the polymer is processed from solution or from the melt, so that the flameproofing agent can be added to this solution or melt. The cellulose xanthogenate solutions which are known as viscose solutions and which are used for the manufacture of fibers and sheets of regenerated cellulose are one example. Solutions of cellulose acetate in organic solvents are another example.

Polyurethanes which can be flameproofed with the compounds of the formula I can be both linear and branched polyurethanes such as are used for the manufacture of films, fibers, brushes, coatings, elastic materials and rigid and soft foam plastics. The flameproofing of polyurethane foam plastics is of particular importance since such foams, like all materials having a large surface area, burn more easily than compact materials.

It is common knowledge that such polyurethane foams or coating compositions are manufactured from polyhydroxy compounds, e.g., polyesters or polyethers which contain hydroxy groups on the one hand and polyisocyanates, e.g., toluene diisocyanate, on the other. The introduction of flameproofing agents of the formula I can be accomplished by adding them to the starting components mentioned hereinbefore, i.e., simultaneously with the manufacture of the polyurethanes, since the oxaphospholane derivatives scarcely influence the pot life and curing time. Non-inflammable polyurethane foam plastics or coatings with excellent mechanical properties and very good resistance to ageing are thereby obtained.

The compounds of the formula I are normally added to the cited substrates in an amount of 2 to 30% by weight, preferably 2 to 10% by weight, based on the substrate. The addition can be carried out before or during the manufacture of the substrate by polymerization; but frequently the compounds are added to the finished polymers before or during their processing.

In addition to the flameproofing agents of formula I, it is also possible to add to the polymeric substrates other flameproofing agents, e.g., organic halogen compounds, antimony oxide or other phosphorus compounds. It is furthermore possible to add other customary and known additives, e.g., antioxidants, heat stabilizers, UV absorbers, fluorescent brighteners, antistatic agents, lubricants, softeners, emulsifiers, pigments, carbon black, asbestos, kaolin, talcum, glass fibers or other fillers and reinforcing agents.

The manufacture and utility of the oxaphospholanes of the formula I are illustrated in more detail in the following examples:

EXAMPLE 1

2-Oxo-2-ethoxy-3,3,5-trimethyl-5-diethylphosphono-1,2-oxaphospholane 10 ml of diethyl phosphite was added to a solution of 98.1 g (1 mole) of mesityl oxide in 300 ml of benzene, and the mixture was then heated to 80° C. About 200 mg of metallic sodium was added to the almost boiling solution, whereupon an exothermic reaction commenced. The reaction was brought to completion over the course of 10 minutes by gradual addition of altogether 345.0 g (2.5 moles) of diethyl phosphite and 4.2 g of sodium. The reaction mixture was stirred for an additional 10 minutes, neutralized with 11 g of glacial acetic and evaporated in vacuum. The residue was distilled in high vacuum. The main fraction distilled as an almost colorless oil at 136°-139° C and 0.035 mm Hg. Analysis by nuclear magnetic resonance and mass spectrum showed this fraction to be 2-oxo-2-ethoxy-3,3,5-trimethyl-5-diethylphosphono-1,2-oxaphospholane of the empirical formula $C_{12}H_{26}O_6P_2$ (MW = 328.29).

Analysis: Calc: C, 43.90; H, 7.99; P, 18.92. Found: C, 44.30; H, 8.00; P, 18.0.

The yield was 45.3% of theory.

The same reaction was carried out with 392 g (4 moles) of mesityl oxide and 1,660 g (12 moles) of diethyl phosphite in 1,200 ml of benzene and in the presence of 9.5 g of sodium. Upon completion of the reaction (40 minutes), the reaction mixture was neutralized with 24.8 g of glacial acetic acid and distilled to yield 995.7 g of 2-oxo-2-ethoxy-3,3,5-trimethyl-5-diethylphosphono-1,2oxaphospholane at 136°-140° C at 0.02-0.04 Torr. This corresponded to a yield of 75.9% of theory.

EXAMPLE 2

2-Oxo-2-methoxy-3,3,5-trimethyl-5-dimethylphosphono-1,2-oxaphospholane

A solution of 30.0 g of sodium methoxide in 90 ml of methanol was added dropwise to a mixture of 220 g of dimethyl phosphite and 98 g of mesityl oxide over the course of 2 hours in such a way that the reaction temperature did not exceed 65° C. The clear solution was subsequently heated for 2 hours to 70° C. The reaction mixture was concentrated in vacuo and the residue was taken up in 200 ml of toluene. The solution was filtered and the filtrate distilled. The 2-oxo-2-methoxy-3,3,5-trimethyl-5-dimethylphosphone-1,2-oxaphospholane distilled at 158°-160° C at 0.6 mm Hg in the form of a colorless, viscous oil.

Analysis for $C_9H_{20}O_6P_2$ (MW = 286.20): Calc: C, 37.80; H, 7.05; P, 21.65. Found: C, 37.79; H, 7.04; P, 21.32.

EXAMPLE 3

2-Oxo-2-tetrahydrofurfuryloxy-3,3,5-trimethyl-5-bis-(tetrahydrofurfuryl)phosphono-1,2-oxaphospholane As described in Example 1, a mixture of 37.6 g of bis-(tetrahydrofurfuryl) phosphite and 4.9 g of mesityl oxide in 80 ml of benzene was reacted by heating in the presence of 1.3 g of sodium over the course of 1 hour. The reaction was vigorously exothermic. The sodium was neutralized by addition of 3.4 g of glacial acetic acid. The inorganic salt was extracted from the mixture with 2 portions of 20 ml of water. The benzene solvent was removed in a rotary evaporator, leaving as residue 32.6 g of crude product which still contained di-tetrahydrofurfuryl phosphite. Distillation of 4.3 g of the crude product in a bulb tube oven in high vacuum yielded the desired product at an oven temperature between 185° C and 230° C and a pressure of 0.01 mm Hg.

Yield: 2.07 grams

Analysis, $C_{21}H_{38}O_9P_2$ (MW = 496.48): Calc: C, 50.8; H, 7.7; P, 12.5. Found: C, 49.5; H, 7.7; P, 12.6.

Although the mass spectrum did not show the molecular peak at m/e 496, it did show instead the M+H peak at m/e 497. Fragments characteristic of this compound occurred at m/e 426 ($M^+$—$C_4H_6O$) and 413 ($M^+$—$C_5H_7O$).

EXAMPLE 4

2-Oxo-2-ethoxy-3,3,5-trimethyl-5-diethylphosphono-1,2-oxaphospholane 98 g of mesityl oxide (1.0 mole) and 415 g of diethyl phosphite (3.0 moles) were dissolved in 300 ml of benzene. 200 ml of this solution was heated to the boiling point. A catalytic amount of sodium was added whereupon a vigorous exothermic reaction commenced, and the mixture boiled by itself after removal of the heating bath. After the sodium dissolved, the reaction came practically to a stop and was initiated again by addition of a further amount of sodium. In this manner sodium was added until the main reaction was over. Then about one third of the remaining solution was added, and this was also reacted as previously by adding sodium. The remaining two thirds of the solution were then reacted in the same way. Altogether 3.0 g of sodium was used over the course of 25 minutes. The entire reaction mixture was allowed to continue to react for 15 minutes at reflux. It was then neutralized with 8 g of glacial acetic acid and diluted with 350 ml of benzene. After the reaction solution cooled, it was washed with two portions of water of 75 and 20 ml respectively. The combined aqueous phases were extracted with 50 ml of benzene twice to give a solution in benzene which was combined with the chief portion, dried with Na$_2$SO$_4$ and concentrated in a rotary evaporator. Distillation yielded 118.5 g of a first fraction of b.p. 46°–68° C/8 mm Hg, which largely consisted of diethyl phosphite, and 280.8 g (85.6% of theory) of the oxaphospholane which boiled at 122°–132° C at 0.008 mm Hg. Gas chromatography showed the product to be about 95% pure. 8.2 g remained as the distillation residue.

EXAMPLE 5

2-Oxo-2-isopropoxy-3,3,5-trimethyl-5-diisopropylphosphono-1,2-oxaphospholane

As described in Example 4, a mixture of 19.6 g of mesityl oxide (0.20 mole), 99.6 g of diisopropyl phosphite (0.60 mole) and 100 ml of benzene was reacted with 2.1 g of sodium as catalyst over the course of 10 minutes. The reaction was vigorously exothermic. After a subsequent reaction for 15 minutes at the boiling temperature, the reaction mixture was neutralized with 5.5 g of glacial acetic acid and diluted with 150 ml of benzene. After the reaction solution cooled, it was extracted with 20 ml of benzene twice, and the extract was combined with the chief portion, dried over Na$_2$SO$_4$ and concentrated in a rotary evaporator. The distillation yielded 27.5 g of a first fraction with a boiling point of 68°–75° C/10 mm Hg and consisting of virtually pure diisopropyl phosphite as well as 58.0 g (78.3%) of the oxaphospholane which boiled at 120°/0.02 mm Hg to 125° C/0.05 mm Hg; 5.3 g remained as residue.

Analysis, for C$_{15}$H$_{32}$O$_6$P$_2$ (MW = 370.37): Calc: C, 48.64; H, 8.71; P, 16.73. Found: C, 48.77; H, 8.92; P, 16.37.

The mass spectrum showed the molecular peak at m/e 370.

EXAMPLE 6

2-Oxo-2-ethoxy-4,5-dimethyl-5-diethylphosphono-1,2-oxaphospholane

In analogous manner to Example 4, a mixture of 25 g of freshly distilled methyl isopropenyl ketone (0.30 mole), 124 g of diethyl phosphite (0.90 mole) and 75 ml of benzene was reacted with 2.5 g of sodium over the course of 10 minutes. The reaction was vigorously exothermic. After a subsequent reaction for 10 minutes at the boiling temperature, the reaction mixture was neutralized with glacial acetic acid and diluted with 300 ml of benzene. After the reaction solution cooled, it was extracted with 60 ml of H$_2$O. The aqueous phase was extracted twice with 60 and 30 ml of benzene respectively, and the extract was combined with the chief portion, dried over Na$_2$SO$_4$ and concentrated in a rotary evaporator. Distillation yielded 49.2 g (52.2% of theory) of the oxaphospholane of b.p. 128°–132° C/0.002 mm Hg.

Analysis, for C$_{11}$H$_{24}$O$_6$P$_2$ (MW = 314.26). Calc: C, 42.04; H, 7.70; P, 19.71. Found: C, 41.78; H, 7.69; P, 19.39.

The mass spectrum showed the molecular peak at m/e 314.

EXAMPLE 7

2-Oxo-2-butoxy-3,3,5-trimethyl-5-dibutylphosphono-1,2-oxaphospholane

A reaction solution was prepared from 194 g (1 mole) of freshly distilled dibutyl phosphite and 32.4 g (0.33 mole) of mesityl oxide in 200 ml of absolute benzene. 30 ml of this mixture was put into the reaction flask and treated with about 50 mg of sodium. An exothermic reaction commenced and the temperature rose to 70° C. After the reaction subsided, the mixture was brought to reflux temperature by addition to the reaction solution in small amounts of 1.5 g sodium. Stirring was continued for 1 hour at 70° C and the reaction mixture was subsequently neutralized with glacial acetic acid. Distillation yielded the product with a boiling point of 158°–162° C/0.01 mm.

EXAMPLE 8

2-Oxo-2-cyclohexoxy-3,3,5-trimethyl-5-dicyclohexylphosphono-1,2-oxaphospholane 88 g (0.35 mole) of freshly distilled dicyclohexyl phosphite was dissolved in 150 ml of absolute benzene, and the solution was warmed to 50° C. After addition of 2 g of sodium, 15 g (0.14 mole) of freshly distilled mesityl oxide was added dropwise. The exothermic reaction caused the temperature of the mixture to rise to 70° C. After termination of the reaction, the reaction mixture was stirred for further 2 hours and then neutralized with glacial acetic acid. The filtered solution was distilled, and the product with a boiling point of 150°–153° C/0.01 mm Hg was obtained.

EXAMPLE 9

2-Oxo-2-ethoxy-3,3,5-trimethyl-5-diethylphosphono-1,2-oxaphospholane 690 g of diethyl phosphite and 50 g of a sodium ethoxide solution (17 g of sodium dissolved in 83 g of ethanol) were mixed and with stirring, 245.5 g of mesityl oxide was dropped into this solution over the course of 40 minutes. During the dropwise addition an exothermic reaction took place, the reaction temperature rising from 20° C to 101° C when up to half the amount of mesityl oxide was added. The temperature then fell to 75° C when the second half of the mesityl oxide was added. The colorless, clear solution was stirred for 50 minutes and the temperature in the reaction mixture fell to 39° C. Then an additional 25 g of sodium ethoxide solution was added all at once, whereupon the temperature of the reaction mixture rose from 39° to 84° C. The reaction mixture was stirred for 30 minutes and then 25 g of sodium ethoxide solution was added. The resultant reaction mixture was stirred for 3 hours at room temperature and subsequently neutralized with 15 g of glacial acetic acid. Distillation of this reaction mixture yielded at 162°–167° C/0.5 mm 626 g of 2-oxo-2-ethoxy-3,3,5-trimethyl-5-diethylphosphono-1,2-oxaphospholane as a colorless liquid. Chromatographic analysis showed a purity of 99.1%.

EXAMPLE 10

2-Oxo-2-ethoxy-5-methyl-5-diethylphosphono-1,2-oxaphospholane 276 g (2 moles) of freshly distilled diethyl phosphite was treated with a solution of 3.5 g of sodium methoxide in 20 ml of absolute ethanol, and 70 g (1 mole) of freshly distilled methyl vinyl ketone was then added dropwise thereto. The exothermic reaction caused the temperature of the mixture to rise to about 70° C. After the whole amount of methyl vinyl ketone was dropped in, stirring was continued for 2½ hours and the reaction mixture was neutralized with glacial acetic acid. After a first fraction which consisted largely of diethyl phosphite and methyl vinyl ketone, the distillation at 0.01 mm yielded the product with a boiling point of 20°–133° C.

EXAMPLE 11

2-Oxo-2-ethoxy-5-ethyl-5-diethylphosphono-1,2oxaphospholane 138 g (1 mole) of freshly distilled diethyl phosphite was treated with a solution of 1.75 g (0.075 mole) of sodium in 10 ml of absolute ethanol, and 42 g (0.5 mole) of ethyl vinyl ketone was then added dropwise thereto. The exothermic reaction caused the temperature of the mixture to rise to 70° C. After the whole amount of ethyl vinyl ketone was dropped in, the reaction was brought to completion by adding another 1 g (0.04 mole) of sodium in 10 ml of absolute alcohol with a rise in temperature to 60° C observed. Stirring was continued for 2 hours and the reaction mixture was then neutralized with glacial acetic acid. After a first fraction which consisted largely of diethyl phosphite and ethyl vinyl ketone, the distillation at 0.1 mm yielded the product having a boiling point of 132°–138° C.

EXAMPLE 12

2-Oxo-2-ethoxy-3-phenyl-5-methyl-5-diethylphosphono-1,2-oxaphospholane 276 g (2 moles) of freshly distilled diethyl phosphite was treated with a solution of 3.5 g (0.15 mole) of sodium in 20 ml of absolute ethanol. At 40° C, 146 g (1 mole) of benzalacetone was dissolved in 50 ml of absolute ethanol, and this solution was added dropwise to the first solution. The exothermic reaction caused the temperature of the mixture to rise to 90° C over the course of 1 hour. After completion of the addition of benzalacetone solution, the reaction mixture was stirred for 3 hours and neutralized with glacial acetic acid. The product was isolated in the subsequent distillation at 187°–210° C/0.01 mm.

EXAMPLE 13

2-Oxo-2-ethoxy-3,3,5-trimethyl-5-diethylphosphono-1,2-oxaphospholane 10 ml of a mixture of 70.8 g of 4-methyl-4-(diethylphosphono)-pentan-2-one (prepared from mesityl oxide and diethyl phosphite) and 82.8 g of diethyl phosphite were dissolved in 100 ml of toluene, and the solution was heated to 80° C. A catalytic amount of sodium was added and a vigorous exothermic reaction commenced. The reaction temperature was held between 80° C and 90° C by alternately adding the previously prepared mixture and small pieces of sodium. Altogether 1.65 g of sodium was used as catalyst. The reaction took 20 minutes. The reaction mixture was subsequently stirred at 80°–90° C for 30 minutes with heating, then cooled and neutralized with 4.5 g of glacial acetic acid. This reaction mixture was distilled to yield 2-oxo-2-ethoxy-3,3,5-trimethyl-5-diethylphosphono-1,2-oxaphospholane with a boiling point of 156°–161° C/1.1 mm. This substance is identical to the oxaphospholane manufactured according to Example 4.

EXAMPLE 14

2-Oxo-2-ethoxy-3,3,5-trimethyl-5-dimethylphosphono-1,2-oxaphospholane

By carrying out the same procedure as described in Example 13, 2-oxo-2-ethoxy-3,3,5-trimethyl-5-dimethylphosphono-1,2-oxaphospholane with a boiling point of 146°–148° C/0.5 mm was obtained from 70.8 g of 4-methyl-4-(diethylphosphono)-pentan-2-one and 66.0 g of dimethyl phosphite with 1.65 g of sodium as catalyst.

EXAMPLE 15

2-Oxo-2-ethoxy-3,3,5-trimethyl-5-diisopropylphosphono-1,2-oxaphospholane

By carrying out the same procedure as described in Example 13, 2-oxo-2-ethoxy-3,3,5-trimethyl-5-diisopropylphosphono-1,2-oxaphospholane with a boiling point of 180°–185° C/2 mm was obtained from 70.8 g of 4-methyl-4-(diethylphosphono)-pentan-2-one and 99.6 g of diisopropyl phosphite with 4.6 g of sodium as catalyst.

EXAMPLE 16

2-Oxo-2-methoxy-3,3,5-trimethyl-5-diethylphosphono-1,2-oxaphospholane

By carrying out the same procedure as described in Example 13, 2-oxo-2-methoxy-3,3,5-trimethyl-5-diethylphosphono-1,2-oxaphospholane with a boiling point of 114°–146° C/0.6 mm was obtained from 83.2 g of 4-methyl-4-(dimethylphosphono)-pentan-2-one and 110.4 g of diethyl phosphite with 1.15 g of sodium as catalyst. The $P^{31}$ spectrum showed for the phosphorus atom in the ring a shift of −48 ppm compared with $H_3PO_4$ as standard.

EXAMPLE 17

2-Oxo-2-ethoxy-3,3,5-trimethyl-5-diisooctylphosphono-1,2-oxaphospholane

By carrying out the same procedure as described in Example 13, 2-oxo-2-ethoxy-3,3,5-trimethyl-5-diisooctylphosphono-1,2-oxaphospholane was obtained as a viscous, colorless oil from 47.2 g of 4-methyl-4-(diethylphosphono)-pentan-2-one and 84.6 g of diisooctyl phosphite with 1.15 g of sodium as catalyst. The $P^{31}$ spectrum of this oil showed for the phosphorus atom in the ring a shift of −49 ppm compared with $H_3PO_4$ as standard.

EXAMPLE 18

2-Oxo-2-ethoxy-3,3,5-trimethyl-5-di-n-octylphosphono-1,2-oxaphospholane

By carrying out the same procedure as described in Example 13, 2-oxo-2-ethoxy-3,3,5-trimethyl-5-di-n-octylphosphono-1,2-oxaphospholane was obtained as a viscous, pale yellow oil from 47.2 g of 4-methyl-4-(diethylphosphono)-pentan-2-one and 84.6 g of di-n-octyl phosphite with 1.15 g of sodium as catalyst. The $P^{31}$ spectrum of this oil showed for the phosphorus atom in the ring a shift of −49 ppm compared with $H_3PO_4$.

EXAMPLE 19

2-Oxo-2-ethoxy-3,3,5-trimethyl-5-bis-(2-chloroethyl)-phosphono-1,2-oxaphospholane By carrying out the same procedure as described in Example 13, 2-oxo-2-ethoxy-3,3,5-trimethyl-5-bis-(2-chloroethyl)phosphono-1,2-oxaphospholane was obtained from 47.2 g of 4-methyl-4-(diethylphosphono)-pentan-2-one and 45.2 g of bis-(2-chloroethyl) phosphite. In the $P^{31}$ spectrum, this compound showed for the phosphorus atom in the ring a shift of $-50.2$ ppm compared with $H_3PO_4$ as standard.

EXAMPLE 20

2-Oxo-2-propyloxy-3,3,5-trimethyl-5-dipropylphosphono-1,2-oxaphospholane 11.8 g of mesityl oxide and 9.8 g of dipropyl phosphite were heated in 40 ml of benzene to 80° C. At this temperature, 0.1 g of sodium was added, whereupon an exothermic reaction commenced. The reaction temperature was held at 80°–90° C without external heating by alternately adding 40.0 g of dipropyl phosphite and 0.4 g of sodium. After all the sodium was added, stirring was continued for 30 minutes. The reaction mixture was then cooled and neutralized with 1.4 g of glacial acetic acid. The reaction mixture was concentrated in a rotary evaporator and then distilled in a high vacuum to yield 2-oxo-2-ethoxy-3,3,5-trimethyl-5-dipropylphosphono-1,2-oxophospholane in the form of a colorless oil with a boiling point of 153°–154° C/0.1 mm. The $P^{31}$ spectrum showed for the phosphorus atom in the ring a shift of $-67.2$ ppm compared with triphenyl phosphate as standard.

EXAMPLE 21

2-Oxo-2-(2-methoxyethoxy)-3,3,5-trimethyl-5-bis-(2-methoxyethyl)-phosphono-1,2-oxaphospholane 15.7 g of mesityl oxide and 9.2 g of bis-(2-methoxyethyl)phosphite were heated to 80° C in 50 ml of benzene. At this temperature, 0.1 g of sodium was added whereupon an exothermic reaction commenced. The reaction temperature was held between 80°–90° C without external heating by alternately adding 70.0 g of bis-(2-methoxyethyl) phosphite and 0.6 g of sodium. After all the sodium was added, the reaction mixture was stirred for 30 minutes at 80° C, cooled and neutralized with 1.75 g of glacial acetic acid. The reaction mixture was concentrated in a rotary evaporator, and the residue was then distilled in a high vacuum to yield 2-oxo-2-(2-methoxyethoxy)-3,3,5-trimethyl-5-bis-(2-methoxyethyl)phosphono-1,2-oxaphospholane in the form of a colorless oil with a boiling point of 193°–196° C/0.07 mm. The $P^{31}$ spectrum showed for the phosphorus atom in the ring a shift of $-67.2$ ppm compared with triphenyl phosphate as standard.

EXAMPLE 22

2-Oxo-2-allyloxy-3,3,5-trimethyl-5-diallylphosphono-1,2-oxaphospholane 11.5 g of mesityl oxide and 7.4 g of diallyl phosphite were heated to 80° C in 40 ml of benzene. At this temperature, 0.1 g of sodium was added. An exothermic reaction started and the reaction temperature was held at 80°–90° C without external heating by alternately adding 40.0 g of diallyl phosphite and 0.4 g of sodium. After all the sodium was added, the reaction mixture was stirred for 30 minutes at 80° C, then cooled and neutralized with 1.3 g of glacial acetic acid. The reaction mixture was concentrated in a rotary evaporator to yield as residue 2-oxo-2-allyloxy-3,3,5-trimethyl-5-diallylphosphono-1,2-oxaphospholane in the form of a pale yellow oil. The $P^{31}$ spectrum showed for the phosphorus atom in the ring a shift of $-68.5$ ppm compared with triphenyl phosphate as standard.

EXAMPLE 23

2-Oxo-2-ethoxy-3-(4-methoxyphenyl)-5-methyl-5-diethylphosphono-1,2-oxaphospholane A mixture was prepared of 69.0 g of diethyl phosphite and 5 g of 17% sodium ethoxide solution in ethanol. To this reaction mixture was added in small amounts 44 g of p-methoxy-benzalacetone, whereupon the temperature rose from 25° C to 89° C. The reaction mixture was stirred for 50 minutes and then a further 2.5 g of the 17% sodium ethoxide solution was added. After an additional 30 minutes, 3.5 g of diethyl phosphite and 2.5 g of sodium ethoxide solution were added to give a pale yellow, clear solution which was concentrated in a rotary evaporator. The $P^{31}$ spectrum for the phosphorus atom in the ring showed a shift of $-58$ ppm compared with triphenyl phosphate.

EXAMPLE 24

2-Oxo-2-ethoxy-3-(4-methylphenyl)-5-methyl-5-diethylphosphono-1,2-oxaphospholane By carrying out the same procedure as described in Example 23, 2-oxo-2-ethoxy-3-(4-methylphenyl)-5-methyl-5-diethylphosphono-1,2-oxaphospholane was obtained from 30.2 g of 4-methyl-benzalacetone and 54.7 g of diethyl phosphite with 7.8 g of a 17% sodium ethoxide solution in ethanol. The $P^{31}$ spectrum of the product showed a shift of $-58$ ppm for the phosphorus atom in the ring.

EXAMPLE 25

2-Oxo-2-ethoxy-3-(4-chlorophenyl)-5-methyl-5-diethylphosphono-1,2-oxaphospholane By carrying out the same procedure described in Example 23, 2-oxo-2-ethoxy-3-(4-chlorophenyl)-4-methyl-5-diethylphosphono-1,2-oxaphospholane was obtained from 45.2 g of 4-chloro-benzalacetone and 72.5 g of diethyl phosphate with 10 g of a 17% sodium ethoxide solution in ethanol. The $P^{31}$ spectrum of the product showed a shift of $-57.5$ ppm for the phosphorus atom in the ring compared with triphenyl phosphate.

EXAMPLE 26

2-Oxo-2-ethoxy-3-furyl-5-methyl-5-diethylphosphono-1,2-oxaphospholane

By otherwise carrying out the same procedure as described in Example 23, 2-oxo-2-ethoxy-3-furyl-5-methyl-5-diethylphosphono-1,2-oxaphospholane was obtained from 34.0 g of furfurylidene acetone and 72.5 g of diethyl phosphite with 10 g of a 17% sodium ethoxide solution in ethanol. The $P^{31}$ spectrum of the product showed a shift of $-55.3$ ppm for the phosphorus atom in the ring compared with triphenyl phosphate.

EXAMPLE 27

Flameproofing of Polyethylene Terephthalate 15 parts of a comercially available polyethylene terephthalate were dissolved in 85 arts of hexafluoroisopropanol. This solution was mixed with the corresponding amount of flameproofing agent and stirred until it was homogeneous. Using a film drawing rod, half of the solution was applied to a glass plate to a thickness of 0.5 mm. A glass cloth was then pressed on the film and was coated by the second half of the solution in a thickness of 1 mm. Drying in vacuo of 120° C over 16 hours was subsequently carried out. The dried film was drawn from the glass plate and the flammability was determined by the LOI method described by C. P. Fenimore and J. F. Martin in "Combustions and Flame" 10, No. 2, 135–139 (June 1966). In this test, a film is ignited in an atmosphere of nitrogen and oxygen of different volume composition and the volume ratio is ascertained at which it is still just possible to maintain combustion of the test specimens. The LOI value is the minimum oxygen concentration in a nitrogen-oxygen mixture at which the specimen just still burns. The higher the LOI value of the lower the flammability of the sheeting, i.e., the more effective is the addition of the flameproofing agent.

| Flameproofing Agent | Amount of Flameproofing Agent* | LOI |
|---|---|---|
| Flameproofing agent according to Example 1 | 5% | 0,225 |
| Flameproofing agent according to Example 1 | 10% | 0,250 |
| Without flameproofing agent | — | 0,200 |

*Based on polyethylene terephthalate

EXAMPLE 28

Flameproofing of a Polyamide 15 parts of a commercially available nylon 6 were dissolved in 85 parts of trifluoroethanol. This solution was mixed with the corresponding amount of flameproofing agent and stirred until homogeneous. Films were prepared in a manner analogous to that described in Example 27 for polyethylene terephthalate and LOI values were determined. The following Table shows how the LOI value increased by addition of the flameproofing agents according to the invention as compared with nylon 6 without flameproofing agent.

| Flameproofing Agent | Amount of Flameproofing Agent* | LOI |
|---|---|---|
| Flameproofing agent according to Example 1 | 5% | 0,216 |
| Flameproofing agent according to Example 1 | 10% | 0,231 |
| Without flameproofing agent | — | 0,196 |

*Based on nylon 6

EXAMPLE 29

Flameproofing of Polyacrylonitrile 201 parts of commercially available polyacrylonitrile were dissolved in 80 parts of dimethylformamide. This solution was mixed with the corresponding amount of flameproofing agent and stirred to homogeneity. Films were prepared in a manner analogous to that described in Example 27 for polyethylene terephthalate and the LOI values were determined. The following Table shows how the LOI value increased by addition of the flameproofing agents according to the invention as compared with polyacrylonitrile without flameproofing agent.

| Flameproofing Agent | Amount of Flameproofing Agent | LOI |
|---|---|---|
| Flameproofing agent according to Example 1 | 5% | 0,207 |
| Flameproofing agent according to Example 1 | 10% | 0,224 |
| Without flameproofing agent | — | 0,189 |

EXAMPLE 30

Flameproofing of a Polyurethane Foam

A soft polyurethane foam was manufactured by mixing the following materials:

- 100 g of a polyhydroxy compound on a polyether basis with a molecular weight of about 3,000 and an OH number of 56
- 1 g of a siloxane-oxyalkylene copolymer
- 0.1 g of tin (II) octoate
- 3.5 g of water
- 48.2 g of toluene diisocyanate (80:20 mixture of 2,4- and 2,5-isomers)
- x g of 2-oxo-2-ethoxy-3,3,5-trimethyl-5-diethylphosphono-1,2-oxaphospholane (compound of Example 1).

The foam so manufactured was tested for its flammability by the ASTM D 1692 test method. For this purpose, test specimens each measuring 150 mm × 50 mm × 13 mm were fixed with the 50 mm × 13 mm surface in the horizontal position. Marks were made at 25 mm and 100 mm. The bottom end of the specimen was then ignited with a gas burner. The ignition time was 60 seconds. The foam was termed flameproof if the burned zone was not longer than 25 mm. If the specimen burned beyond the 25 mm mark and the burned zone was smaller than 125 mm, then the foam was termed self-extinguishing. The length of the burned zone was indicated in mm. If the specimen burned beyond the 125 mm mark, the foam was termed combustible.

| Amount of x g of flameproofing agent/100 g of polyol | None | 6 g | 4 g |
|---|---|---|---|
| a) Foaming behavior | | | |
| - creaming time in seconds | 10 | 13 | 12 |
| - rise time in seconds | 90 | 105 | 128 |
| - time in minutes until foam is no longer tacky | 10 | 3 | 2 |
| b) Flammability (ASTM D 1692) | | | |
| - burned in mm | 150 | 45 | 55 |
| - rate of combustion in mm/sec. | 1.8 | 1.0 | 1.5 |

Individual foam specimens were also subjected to the flameproofing test after an ageing at 140° C dry and 90° C humid over the course of 1, 2, 4 and 7 days.

|  | Burned zone in mm with 6 g of flameproofing agent/ 100 g of polyol | Burned zone in mm with 4 g of flameproofing agent/ 100 g of polyol |
| --- | --- | --- |
| Storage conditions 140° dry |  |  |
| After 1 day | 85 | 60 |
| After 2 days | 120 | 60 |
| After 4 days | 35 | 50 |
| After 7 days | 60 | 50 |
| Storage conditions 90° C humid |  |  |
| After 1 day | 40 | 45 |
| After 2 days | 60 | 50 |
| After 4 days | 60 | 45 |
| After 7 days | 65 | 45 |

These figures show that a storage resistant flameproofing was obtained with 2-oxo-2-ethoxy-3,3,5-trimethyl-5-diethylphosphone-1,2-oxaphospholane even if only 4 g of this compound per 100 g of polyol was used.

What is claimed is:

1. A method of flameproofing thermoplastic polymers, polyurethanes, cellulose or cellulose derivatives which comprises adding to the polymer at least one compound of formula I

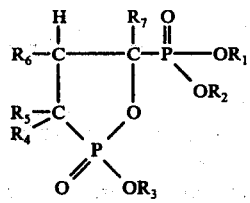

wherein
each of $R_1$, $R_2$ and $R_3$ independently represents alkyl with 1 to 18 carbon atoms, haloalkyl or alkoxyalkyl having not more than 18 carbon atoms, alkenyl with 3 to 18 carbon atoms, tetrahydrofurfuryl, aralkyl with 7 to 15 carbon atoms, or aralkyl with altogether 7 to 15 carbon atoms which is substituted by halogen or alkoxy of 1 to 4 carbon atoms, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups with 1 to 4 carbon atoms or represents 2-furyl, 2-thienyl or 2-pyridyl, $R_6$ represents hydrogen, methyl or phenyl, and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms or represents 2-furyl, 2-thienyl or 2-pyridyl.

2. A method according to claim 1, using a compound of formula I wherein each of $R_1$ and $R_2$ independently represents alkyl with 1 to 18 carbon atoms, haloalkyl or alkoxyalkyl having not more than 18 carbon atoms, alkenyl with 3 to 18 carbon atoms, tetrahydrofurfuryl, cycloalkyl with 5 to 8 carbon atoms, aralkyl with 7 to 15 carbon atoms or aralkyl with altogether 7 to 15 carbon atoms which is substituted by halogen or alkoxy of 1 to 4 carbon atoms, $R_3$ is the same as $R_1$ or $R_2$, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups of 1 to 4 carbon atoms, or represents 2-furyl, 2-thienyl or 2-pyridyl, $R_6$ represents hydrogen, methyl or phenyl and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms, or represents 2-furyl, 2-thienyl or 2-pyridyl.

3. A method according to claim 1 using a compound of formula 1 wherein $R_1$, $R_2$ and $R_3$ are identical and represent linear or branched alkyl radicals with 1 to 8 carbon atoms, alkoxyalkyl with 3 to 6 carbon atoms, 2-chloroethyl, 2-bromoethyl, alkenyl with 3 or 4 carbon atoms, cyclohexyl, benzyl or tetrahydrofurfuryl, $R_4$ represents hydrogen or methyl, $R_5$ represents hydrogen, methyl, ethyl, phenyl, naphthyl, phenyl or naphthyl substituted with 1 to 5 chlorine or bromine atoms, p-tolyl, xylyl, p-anisyl, 2-furyl, 2-thienyl or 2-pyridyl, $R_6$ represents hydrogen or methyl, and $R_7$ represents methyl, ethyl, phenyl, phenyl substituted with 1 to 5 chlorine or bromine atoms, p-tolyl, xylyl, p-anisyl, 2-furyl or 2-thienyl.

4. A method according to claim 1, which comprises adding the flameproofing agent during the manufacture of the polymers.

5. A method according to claim 1, which comprises adding the flameproofing agent during the manufacture of polyurethane foams made from polyisocyanates and polyhydroxy compounds.

6. A flame resistant thermoplastic polymer, polyurethane, cellulose or cellulose derivative which contains at least one compound of formula I according to claim 1

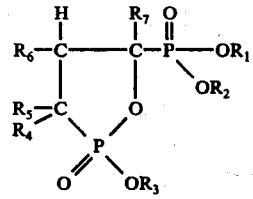

wherein each of $R_1$, $R_2$ and $R_3$ independently represents alkyl with 1 to 18 carbon atoms, haloalkyl or alkoxyalkyl having not more than 18 carbon atoms, alkenyl with 3 to 18 carbon atoms, tetrahydrofurfuryl, aralkyl with 7 to 15 carbon atoms, or aralkyl with altogether 7 to 15 carbon atoms which is substituted by halogen or alkoxy of 1 to 4 carbon atoms, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups with 1 to 4 carbon atoms or represents 2-furyl, 2-thienyl or 2-pyridyl, $R_6$ represents hydrogen, methyl or phenyl, and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms, or represents 2-furyl, 2-thienyl or 2-pyridyl.

7. A flame resistant thermoplastic polymer, polyurethane, cellulose or cellulose derivative according to claim 6 which contains at least one compound of formula I wherein each of $R_1$ and $R_2$ independently represents alkyl with 1 to 18 carbon atoms, haloalkyl or alkoxyalkyl having not more than 18 carbon atoms, alkenyl with 3 to 18 carbon atoms, tetrahydrofurfuryl, cycloalkyl with 5 to 8 carbon atoms, aralkyl with 7 to 15 carbon atoms or aralkyl with altogether 7 to 15 carbon atoms which is substituted by halogen or alkoxy of 1 to 4 carbon atoms, $R_3$ is the same as $R_1$ or $R_2$, $R_4$ represents hydrogen or methyl, $R_5$ represents hydrogen, alkyl with 1 to 8 carbon atoms, aryl with 6 to 10 carbon atoms, aryl with 6 to 10 carbon atoms which is substituted by halogen, alkyl or alkoxy groups of 1 to 4 carbon atoms, or represents 2-furyl, 2-thienyl or 2-pyridyl, $R_6$ represents hydrogen, methyl or phenyl and $R_7$ represents alkyl with 1 to 8 carbon atoms, aryl with 6 to 10 carbon atoms, aryl with 6 to 10 carbon atoms which is substituted by halogen, alkyl or alkoxy groups with 1 to 8 carbon atoms, or represents 2-furyl, 2-thienyl or 2-pyridyl.

8. A flame resistant thermoplastic polymer, polyurethane, cellulose or cellulose derivative according to claim 6 which contains at least one compound of formula I wherein $R_1$, $R_2$ and $R_3$ are identical and represent linear or branched alkyl radicals with 1 to 8 carbon atoms, alkoxyalkyl with 3 to 6 carbon atoms, 2-chloroethyl, 2-bromoethyl, alkenyl with 3 to 4 carbon atoms, cyclohexyl, benzyl or tetrahydrofurfuryl, $R_4$ represents hydrogen or methyl, $R_5$ represents hydrogen, methyl, ethyl, phenyl, naphthyl, phenyl or naphthyl substituted with 1 to 5 chlorine or bromine atoms, p-tolyl, xylyl, p-anisyl, 2-furyl, 2-thienyl or 2-pyridyl, $R_6$ represents hydrogen or methyl, and $R_7$ represents methyl, ethyl, phenyl, phenyl substituted with 1 to 5 chlorine or bromine atoms, p-tolyl, xylyl, p-anisyl, 2-furyl or 2-thienyl.

9. A flame resistant polyurethane foam according to claim 8.

10. A method according to claim 1 wherein the compound of formula I is 2-oxo-2-ethoxy-3,3,5-trimethyl-5-diethylphosphono-1,2-oxaphospholane.

11. A flame resistant polymer according to claim 6 wherein the compound of formula I is 2-oxo-2-ethoxy-3,3,5-trimethyl-5-diethylphosphono-1,2-oxaphospholane.

* * * * *